United States Patent

Mukaida et al.

Patent Number: 6,156,678
Date of Patent: Dec. 5, 2000

[54] WATER ABSORBING AGENT ABSORBENT MATERIAL

[75] Inventors: Shingo Mukaida; Tsuyoshi Yuki; Kenji Tanaka, all of Shiga-ken, Japan

[73] Assignee: Sanyo Chemical Industries, Ltd., Kyoto-fu, Japan

[21] Appl. No.: 08/956,488

[22] Filed: Oct. 23, 1997

[30] Foreign Application Priority Data

| Nov. 6, 1996 | [JP] | Japan | 8-311280 |
| May 14, 1997 | [JP] | Japan | 9-141011 |

[51] Int. Cl.$^7$ .................................................... B32B 5/02
[52] U.S. Cl. .................... 442/118; 442/393; 604/358; 604/367; 604/368; 428/402
[58] Field of Search ................... 428/327, 402, 428/403; 604/358, 367, 368; 442/118, 393

[56] References Cited

U.S. PATENT DOCUMENTS

| 4,600,458 | 7/1986 | Kramer et al. | 156/199 |
| 5,047,023 | 9/1991 | Berg | 604/368 |
| 5,505,718 | 4/1996 | Roe et al. | 604/368 |
| 5,714,156 | 2/1998 | Schmidt et al. | 424/404 |

FOREIGN PATENT DOCUMENTS

| 0 304 319 | 2/1989 | European Pat. Off. |
| 0 472 362 A1 | 2/1992 | European Pat. Off. |
| 0 472 362 S1 | 2/1992 | European Pat. Off. |
| 0 697 217 A1 | 2/1996 | European Pat. Off. |
| 0 691 133 | 10/1996 | European Pat. Off. |
| 196 04 601 | 8/1996 | Germany. |
| 1-132802 | 5/1989 | Japan. |
| 7-88171 | 4/1995 | Japan. |
| 8-289903 | 11/1996 | Japan. |

*Primary Examiner*—Paul Thibodeau
*Assistant Examiner*—D. Lawrence Tarazano
*Attorney, Agent, or Firm*—Merchant & Gould P.C.

[57] ABSTRACT

A water absorbing agent comprising water absorbent resin particles having a particle size of 1000 $\mu$m or less, with a two-peak mode particle size distribution, which has an inflection point in the range of 750 to 250 $\mu$m particle size prepared by plotting the mass cumulative content percentage from the larger side of the particle size of the particle size distribution on a logarithmic normal probability paper; and an absorbent material utilizing the water absorbing agent. Since the water absorbing agent of the present invention applied in an absorbent material can realize excellent absorption rate of a liquid and planar diffusion, an absorbent material with an excellent surface dryness can be obtained even for a long time use or when the ratio of the water absorbent resin is high due to a thin shape of the product, without the risk of leakage. Accordingly, the water absorbing agent of the present invention can be preferably used in an absorbent material such as a disposable diaper.

4 Claims, 2 Drawing Sheets

WATER ABSORBING AGENT ABSORBENT MATERIAL

BACKGROUND OF THE INVENTION

1. Field of the Invention

The present invention relates to a water absorbing agent and an absorbent material. More specifically, it relates to a water absorbing agent with excellent absorption rate (initial absorbency) and planar diffusion of an absorbed liquid to provide an excellent surface dry feeling when used in an absorbent material, and an absorbent material using the water absorbing agent.

2. Description of the Prior Art

An absorbent material conventionally used comprises at least a liquid-permeable top sheet, a liquid-impermeable back sheet, and an absorbent layer containing a water absorbent resin and a fibrous material provided between the top and back sheets for absorbing and retaining a liquid. In order to improve the performance of absorbent materials using water absorbent resins, various proposals have been made, aimed at improving the feeling of surface dryness after absorbing a body fluid such as urine and blood, and reduction of leakage. Various ideas have been introduced in many aspects, including improvement of the surface non-woven fabric, arrangement of a water absorbent resin in the absorbent layer, ratio of a water absorbent resin and a fibrous material, application of a hydrophilic diffusion sheet such as a non-woven fabric or a water absorbing paper, and introduction of the embossing treatment of an absorbent layer and variation of the pattern of the embossing. However, these have not yielded a satisfactory result.

Particularly in recent years, since a higher ratio of a water absorbent resin to a fibrous material is provided in an absorbent layer and the weight of the absorbent layer is reduced (the amount of the fibrous material is reduced and the amount of the water absorbent resin is increased) to make the absorbent material thinner and light weight, the efficient use of whole area of absorbent layer is an important element.

In particular, improvement in the absorption rate and the planar diffusion of a liquid to be absorbed is the key for the improvement in the feeling of surface dryness after absorption, and the reduction of leakage.

Efforts have been made to improve diffusion of a liquid by improving a water absorbent resin in an absorbent layer, such as:

① modifying a water absorbent resin or an absorbent layer with a silicone oil modified by ethylene oxide to apply hydrophilic characteristics as disclosed in JP-8-289903-A, ② using a water absorbing agent comprising a water absorbent resin with a comparatively coarse particle size of 400 to 1680 μm in the mass median particle size as disclosed in JP-A-1-132802, and ③ improving the diffusion of a liquid by increasing the gel strength and preventing the gel blocking by the use of a mixture of silicon dioxide and a water absorbent resin crosslinked by a first crosslinking agent having at least two double bonds copolymerizable with acrylic acid and a second crosslinking agent having at least two functional groups reactive with a carboxylic acid group as disclosed in JP-A-7-88171.

However, in the case of the above-mentioned item ①, the need of an extra process of treating with the modified silicone oil causes problems of complicating the process and cost increase.

In the case of the item ②, although it is effective to some extent in terms of the diffusion of a liquid, the absorption rate of the water absorbent resin itself is deteriorated due to the large particle size, and thus it involves a problem of insufficient dry feeling after the diffusion of the liquid.

In the case of the item ③, since the crosslinking degree needs to be increased in general, for increasing the gel strength, the absorbency of the water absorbent resin decreases so that a large amount of the water absorbing agent is required for obtaining the absorbing capacity necessary for an absorbent material, and thus it is not economical.

SUMMARY OF THE INVENTION

Accordingly, an object of the present invention is to provide a water absorbing agent having excellent absorption rate of a liquid and planar diffusion with a good surface dry feeling without the risk of leakage even when used for a long time or used for a thin type absorbent material including a high ratio of a water absorbent resin, and an absorbent material using the water absorbing agent.

That is, the present invention provides a water absorbing agent comprising water absorbent resin particles (A) of a particle size of 1000 μm or less with a two-peak mode particle size distribution, and having an inflection point in the range of 750 to 250 μm particle size prepared by plotting the mass cumulative content percentage from the larger side of the particle size of the particle size distribution on a logarithmic normal probability paper. The present invention provides an absorbent material comprising a liquid-permeable top sheet, a liquid-impermeable back sheet, and an absorbent layer provided between the top and back sheets, wherein the absorbent layer comprises the above mentioned water absorbing agent and a fibrous material (B) with a ratio of (A) to (B) being from (15 to 70):(85 to 30) based on the mass.

DESCRIPTION OF THE PREFERRED EMBODIMENT

Examples of the water absorbent resin (A) in the present invention include crosslinked copolymers of starch-acrylic acid salt, crosslinked polyacrylic acid salt, self-crosslinked polyacrylic acid salt, saponified crosslinked copolymers of acrylate-vinyl acetate, crosslinked copolymers of isobutylene-maleic anhydride, crosslinked polysulfonates, crosslinked copolymers of polyacrylic acid saltpolysulfonate and modified cellulose derivatives. They are particles having a particle size of 1000 µm or less.

A hydrophilic crosslinked polymer mainly comprising carboxylate and/or carboxylic acid, which can absorb and retain a large amount of a liquid by the ionic osmotic pressure with little risk of water release when load or external force is applied thereon, is preferably used. An absorbent resin is water-swellable but essentially is water-insoluble.

In particular, a resin obtained by surface crosslinking of water absorbent resin particles with a crosslinking agent having at least two functional groups reactive with a carboxylic acid group in the water absorbent resin (such as polyglycidyl ether compounds, polyol compounds, polyamine compounds, polyvalent metal salt compounds) in an ordinary method can be preferably used in the present invention.

When the above-mentioned salts of acrylic acid or sulfonic acid are used, the kind and the neutralization degree of the salts are not particularly limited, but the salts preferably used include alkali metal salts such as sodium and potassium, and the neutralization degree is preferably in the range of 50 to 90 mole %, more preferably 60 to 80 mole %.

The water absorbent resin particles (A) in the present invention are particles having a particle size of 1000 µm or less. A particle size larger than 1000 µm may cause problems such as thrusting through the liquid-impermeable back sheet and deteriorating the touch or feeling of the absorbent material. Furthermore, it involves a problem of slowing down the absorption rate of the water absorbent resin itself.

As a water absorbing agent of the present invention, the water absorbent resin particles (A) need to have a two-peak mode particle size distribution, and have an inflection point in the range of 750 to 250 µm particle size, prepared by plotting the mass cumulative content percentage from the larger side of the particle size of the particle size distribution on a logarithmic normal probability paper.

The "particle size" herein is defined such that a particle, which passes through a sieve of a mesh size (E) but does not pass through a sieve of a mesh size (F) smaller than the size (E), has a particle size (X) between the mesh size E and the mesh size F according to the JIS R6002.

"Plotting in a logarithmic normal probability paper" herein denotes the operation of plotting the coordinates of the water absorbent resin particles (A) classified by the JIS mesh based on the JIS Z8101 by having the size of each particle as X (the horizontal axis of the logarithmic normal probability paper) and having the mass cumulative content percentage from the larger side of the particle size as Y (the vertical axis of the logarithmic normal probability paper), and linking the plotted points with a line.

If the curved line drawn by the plotting has an inflection point, the particle size distribution of the water absorbent resin particles has at least two peaks, that is, it is a two-peak mode particle size distribution. If a water absorbent resin has a one-peak mode similar to the normal distribution of ordinary water absorbent resin particles, an inflection point does not exist.

In the case of a one-peak mode particle size distribution observed in conventional water absorbent resin particles, since the particles have a distribution substantially continuously from fine particles to coarse particles, such conventional water absorbent resin particles used in an absorbent material assume a substantially closest packing configuration, so that it is difficult to improve both the absorption rate and the diffusion of a liquid.

That is, a finer particle size, which can contribute to accelerating the absorption rate in the vertical direction, results in a worse diffusion in the lateral direction (horizontal direction) so that the whole area of absorbent layer cannot be used efficiently.

On the other hand, a coarser particle size, which can contribute to improving diffusion in the lateral direction, tends to reduce the absorption rate. In the case of a two-peak mode particle size distribution as in the present invention, since coarse particles and fine particles can be arranged discontinuously so that a gap can be ensured among particles, both the permeation of a liquid (absorption rate) and diffusion in the lateral direction can be improved.

In particular, a two-peak mode particle size distribution separated into two peaks comprising the coarse particle side and the fine particle side at 500 µm as a boundary, that is, the center of the size of particles having 1000 µm or less is preferable. Owing to the two-peak mode particle size distribution mentioned above, both the permeation of a liquid (absorption rate) and the diffusion in the lateral direction can be further improved.

A preferable content by mass at the peak and the nadir of the two peak mode particle size distribution comprises 20 to 80% by mass of particles having a particle size of 1000 (inclusive) to 500 (inclusive) µm and 20 to 80% by mass of particles having a particle size of less than 500 µm, and less than 20% by mass of particles having a particle size in the range of 600 µm (exclusive) to 400 µm (inclusive). A more preferable particle size distribution comprises 15 to 75% by mass of particles having a particle size of 1000 µm (exclusive) to 600 µm (inclusive), 15 to 70% by mass of particles having a particle size of 400 µm (exclusive) to 100 µm (inclusive), less than 5% by mass, particularly preferably less than 2% by mass, of particles having a particle size of less than 100 µm, and less than 20% by mass of particles having a particle size in the range of 600 µm (exclusive) to 400 µm (inclusive).

By having coarse particles and fine particles with such a particle size distribution, a proper discontinuous arrangement having a proper gap among particles can be realized so that an absorbent material having the water absorbing agent of the present invention used in the absorbent layer can satisfy both the quick diffusion in the lateral direction and the rapid absorption in the vertical direction.

When particles having a particle size of 1000 (inclusive) to 500 (inclusive) µm are contained at less than 20% by mass, since the content of particles having a particle size of less than 500 µm increases relatively, although the absorption rate is accelerated, it tends to generate a gel blocking effect so that the water absorbing agent used in an absorbent material tends to prevent diffusion of a liquid. Therefore, not only the whole area of the absorbent layer cannot be utilized effectively but also leakage tends to occur easily.

On the other hand, when particles having a particle size of 1000 (inclusive) to 500 (inclusive) µm are contained at more than 80% by mass, since the content of coarse particles increases relatively, the absorption rate of the water absorbent resin tends to slow down so that the water absorbing agent used in an absorbent material cannot provide a sufficient feeling of surface dryness after liquid absorption or tends to easily generate leakage.

Further, when particles having a particle size of 600 $\mu$m (exclusive) to 400 $\mu$m (inclusive) are contained at 20% or more by mass, the characteristics of a two-peak mode distribution including a good liquid diffusion and a rapid absorption rate cannot be performed properly since it tends to be similar to the conventional one-peak mode distribution.

Further, when particles having a particle size of less than 100 $\mu$m are contained at more than 5% by mass, gel blocking tends to be generated easily and the liquid diffusion cannot be sufficient. Further it may lead to problems including environmental deterioration by flying fine particles during the production of disposable diapers and the like, and clogging the production apparatus, such as screen mesh.

The shape of the water absorbent resin particles (A) is not particularly limited and thus any shape including powder, granule, agglomerate, lamella, flake, lump, sphere can be used. Among these examples, powder, granule, lamella and lump, which can be obtained in an ordinary pulverizing operation, are preferable.

The water absorbent resin particles (A) preferably have an absorbency under load and an absorbency under a pressure free state with respect to physiological saline solution of 40 g/g or more and 20 g/g or more, respectively, and a gel elasticity modulus for a 40-times swelled gel after absorbing physiological saline of 2000 N/m$^2$ or more. In particular, one having an absorbency under a pressure free state of 45 to 75 g/g, an absorbency under load of 25 to 55 g/g, and a gel elasticity modulus of 2500 to 15000 N/m$^2$ is preferable.

By the use of a water absorbent resin having an absorbency under a pressure free state of 40 g/g or more, the water absorbent resin need not be used in a large amount in an absorbent material for ensuring a certain level of absorption performance, and thus it is economical and preferable.

By the use of a water absorbent resin having an absorbency under load of 20 g/g or more, the water absorbent resin need not be used in a large amount in an absorbent material for ensuring a certain level of absorption performance under load, and thus it is economical. The absorbency herein denotes the mass (g) of the physiological saline solution absorbed by a water absorbent resin of 1 g by mass.

By the use of a water absorbent resin having a gel elasticity modulus of 2000 N/m$^2$ or more, since a swelled gel is not too soft and thus the swelled gel is not deformed by load or external stress and there is little risk of adhesion of the swelled gel particles with each other to cause blocking, the permeation of a liquid (absorption rate) or diffusion is not prevented and thus it is preferable.

By having the above mentioned three elements in a good balance, a water absorbing agent used in an absorbent material can perform well and can be economical, and thus it is preferable.

The gel elasticity modulus after shearing of a 40-times swelled gel of (A) after absorbing physiological saline is preferably 1500 N/m$^2$ or more, more preferably 2000 to 13000 N/m$^2$, further preferably 2500 to 10000 N/m$^2$.

By having the gel elasticity modulus after shearing in the above-mentioned range, deformation or destruction of a water absorbed gel is not likely even if shearing stress is applied to the water absorbed gel. Thus the repeated absorption performance of an absorbent material in use over a long time can be excellent with a good dry feeling without the risk of leakage, and thus it is preferable.

The particle size distribution, the absorbency under load, the absorbency under pressure free state, the gel elasticity modulus of 40-times swelled gel with physiological saline solution and the gel elasticity modulus after shearing of water absorbent resin particles are measured by the below-mentioned methods.

Particle size distribution: The particle size distribution is measured according to the JIS R6002. That is, JIS standard sieves with necessary mesh openings are prepared and placed one upon another on a saucer successively from one having the smallest mesh opening. After placing 50 g of a specimen into the uppermost sieve, the saucer and sieves are shaken by a sieve shaker (such as Ro-Tap type D-A produced by IIDA Manufacturing Co. Ltd.) for 5 minutes. The mass of particles on each sieve is measured and the mass ratio thereof is calculated as a percentage with respect to the entire mass of the specimen.

Absorbency under a pressure free state: 1.00 g of water absorbent resin particles were placed in a tea bag of a 10×20 cm size (disclosed in the JIS K7223) made of a 255 mesh nylon fabric and soaked in an excess amount of physiological saline solution (0.9% by mass aqueous solution of sodium chloride) for 60 minutes. Then the tea bag was hung vertically for draining solution off for 15 minutes. The increased mass was measured and the value was defined as the absorbency under a pressure free state.

Absorbency under load: 0.100 g of water absorbent resin particles were placed in a plastic cylinder with a nylon fabric of 255 mesh attached on the bottom (inner diameter 28 mm, height 50 mm) and spread evenly. A weight with an outer diameter of 28 mm was placed thereon such that a load of 20 g/cm$^2$ is applied. The cylinder was placed on the center of a Petri dish (diameter 11 cm) containing 25 ml of physiological saline solution with the nylon fabric side as the bottom side. After soaking for 60 minutes, 10 times the value of the increased mass was defined as the absorbency under load.

Gel elasticity modulus: The compressed deformation ratio was determined by applying a certain load on a swelled gel. Specifically, a 40-times swelled gel was produced by having 1.00 g of water absorbent resin particles absorb 40 ml of physiological saline solution. 0.200 g of the swelled gel was placed evenly at the center of the supporting table of a rheology measuring device (such as Creep Meter RE-33005 produced by YAMADEN Co. Ltd.). By applying a 30 g stress (P=30×98/S) on the upper surface of the swelled gel, the deformation ratio when compressed with a cylinder (H=height at the time of being compressed/initial height) was evaluated. The cross-sectional area thereof {S=sample volume/(initial height—height at the time of being compressed)} was measured. The gel elasticity modulus was sought by the following formula:

Gel elasticity modulus $(N/m^2)=P/H$

Gel elasticity modulus after shearing: 1.00 g of water absorbent resin particles were placed in a 50 ml glass bottle with an airtightly sealable stopper for absorbing 40 ml of physiological saline solution to prepare a 40-times swelled gel, then sealed tightly. The glass bottle was placed in a constant temperature vessel at 40° C. and maintained for 5 hours. After maintaining the temperature for 5 hours, 0.100 g of the gel was placed at the center of the supporting table of a rheology measuring device (such as Creep Meter RE-33005 produced by YAMADEN Co. Ltd.). By repeating vertical movements (going up and down) of the cylinder, compression was repeated for 20 times. The stress after compressing 20 times (F) and the cross-sectional area of the compressed gel (S) were measured. The gel elasticity modulus after shearing was determined by the following formula by calculating the stress with respect to a unit area after shearing:

Gel elasticity modulus after shearing $(N/m^2)=F \times 98/S$.

As a method for obtaining the water absorbent resin particles (A) having a two-peak mode particle size distribution, the following methods can be presented.

① Water absorbent resin particles coarsely pulverized with a first pulverizer were sifted with an 18 mesh sieve (mesh opening: 850 µm) and a 26 mesh sieve (mesh opening: 600 µm) so as to obtain water absorbent resin particles of 18 mesh pass and 26 mesh on (L). "18 mesh pass and 26 mesh on" here denotes particles having a particle size, to pass through an 18 mesh sieve but not pass through a 26 mesh sieve.

The particles larger than 18 mesh were returned to the first pulverizer and pulverized again.

The particles passed through the 26 mesh sieve were pulverized with a second pulverizer. The pulverized particles were sifted with a 36 mesh sieve (mesh opening: 425 µm) and a 100 mesh sieve (mesh opening: 150 µm) so as to obtain water absorbent resin particles of 36 mesh pass and 100 mesh on (S).

The particles of 26 mesh pass and 36 mesh on were returned to the second pulverizer and pulverized again.

The particles (L) and (S) obtained in the above-mentioned processes were mixed by the in-line blending so as to prepare particles with a two-peak mode distribution. The "in-line blending" herein denotes continuous mixing of two or more kinds of particles with a blender (such as a ribbon blender) arranged in the transportation line.

② Among pulverized water absorbent resin particles classified by passing four kinds of sieves, that is, 18 mesh, 26 mesh, 36 mesh and 100 mesh, those at the coarse particle side (L) of 18 mesh pass to 26 mesh on and those at the fine particle side (S) of 36 mesh pass to 100 mesh on were blended to have a product with a two-peak mode distribution.

The remaining particles of 26 mesh pass to 36 mesh on may be pulverized again with another pulverizer to obtain fine particles (S) of 36 mesh pass and 100 mesh on so as to be used in a product, or can be removed to outside the system.

③ Fine particles (S) of 36 mesh pass and 100 mesh on were granulated to have coarse particles (L) of 18 mesh pass and 26 mesh on and mixing (L) and (S) to have a product.

The above-mentioned methods are some examples for industrially manufacturing a product with a two-peak mode particle size distribution, and thus a water absorbing agent of the present invention is not limited thereto.

The positions of the two peaks in the particle size distribution, the ratio of coarse particles and fine particles, the position of the nadir, or the contents of the coarse particles and the fine particles can vary by changing the kind or operation condition of pulverizers, the kind of sieves to be used, or the ratio of (L) and (S).

Pulverizers to be used are not particularly limited and any type, such as a roll mill, a pin-mill, a hammer mill, and a speed mill, can be used alone or in combination of two or more according to the intended two-peak mode distribution.

Silica, zeolite, antioxidants, surfactants, silicone oils, perfumes, disinfectants, and deodorants may be added as an additive or an extender to a water absorbing agent of the present invention in an optional process as needed.

As a fibrous material (B) used in an absorbent layer between a liquid-permeable top sheet and a liquid-impermeable back sheet in an absorbent material applied with a water absorbing agent of the present invention, those conventionally used in an absorbent material, such as fluff pulps and cotton-like pulps can be used.

The raw material (coniferous wood or dicotyledonous wood), the production method (chemical pulp, semi-chemical pulp, CTMP (chemithermomechanical pulp)), and the bleaching method are not particularly limited.

Synthetic fibers that are nonswellable in water can be used as needed. Examples thereof include polyolefin fibers (such as polyethylene fibers, and polypropylene fibers), polyester fibers (such as polyethylene terephthalate fibers, and polyethylene terephthalate-polyethylene isophthalate copolymer fibers), polyolefin-polyester conjugated fibers, polyamide fibers, and polyacrylonitrile fibers. Among these examples, polyolefin fibers, polyester fibers, and blended fibers thereof are preferable. Further preferable are heat-adhesive conjugated fibers comprising a resin component with a low melting point or a low softening point as one component of a sheath & core type conjugated fiber, an eccentric core-sheath type conjugated fiber and a side-by-side type conjugated fiber.

The length and the diameter of the fibrous materials (B) are not particularly limited, but in general, a length of 1 to 200 mm, and a fineness of 0.1 to 100 denir are preferable.

The shape is not particularly limited as long as it is a fiber, and examples thereof include web type, narrow cylindrical type, cut split yarn type, staple type, and filament type.

The amount of a water absorbing agent of the present invention in an absorbent layer is, in general, 15 to 70% by mass with respect to the total amount including the fibrous material (B). It is preferably 20 to 65% by mass, more preferably 30 to 65% by mass.

With less than 15% by mass of a water absorbing agent, a good performance can be achieved even with conventional water absorbent resin particles having a one-peak mode particle size distribution and thus it is not intended in the present invention. Besides, it is difficult to obtain a thin water absorbent material with a high absorbency since the amount of the water absorbing agent is too low. On the other hand, with more than 70% by mass of the water absorbing agent, the diffusion of a liquid becomes insufficient and the absorption rate of the liquid becomes slow. Furthermore, the water absorbing agent tends to be distributed unevenly or to easily fall off or separate from the absorbent layer, and the strength of the absorbent layer declines.

The amount of the water absorbing agent and the fibrous material (B) per water absorbent material is not particularly limited. For a disposable diaper for an infant, in general, the amount of the water absorbing agent is 5 to 15 g, and the amount of (B) is 5 to 30 g. For a thin type disposable diaper, in general, the amount of the water absorbing agent is 7 to 15 g, and the amount of (B) is 7 to 20 g, more preferably the amount of (A) is 8 to 15 g, and the amount of (B) is 8 to 15 g. With the amount of the water absorbing agent in the above-mentioned range, the water absorbing agent can be fixed to the fibrous material sufficiently, and the necessary absorbency can be ensured without ruining the mechanical strength of the absorbent layer. Besides, since an excessive amount of the water absorbent agent is not required, it is economical.

Since the above-mentioned is an example of the water absorbing agent used for a disposable diaper for an infant, the amount of the water absorbing agent and the amount of the fibrous material (B) can vary depending on the application purpose of the absorbent material, the size, or the desired absorbency for the use in a sanitary napkin, a disposable diaper for an adult, or an incontinence pad.

As a method for producing an absorbent layer utilizing a water absorbing agent and a fibrous material (B) of the present invention, the following can be disclosed:

(1) a method of mixing a water absorbing agent and (B) at the same time, (2) a method of forming a layer of (B), spreading a water absorbing agent thereon, and further superimposing a layer of (B) so as to interpose the water absorbing agent between the layers of (B), (3) a method of spreading a water absorbing agent on the mixture layer of (1), and further superimposing a layer of (B) thereon so as to have a multi-layer structure, and (4) a method of forming a (B) layer, superimposing a mixture layer of a water absorbing agent and (B) thereon, and further superimposing a layer of (B) thereon as needed. A device to be used in the production of an absorbent layer is not particularly limited and an ordinary device can be used. Examples thereof include a drum-forming type device.

Other substances may be added within the range not to ruin the effect of the present invention. For example, an absorbent layer can be treated as needed with an alkyl phosphate type anionic surfactant as an anti-static agent; a quaternary ammonium salt type or alkyl imidazolinium salt type cationic surfactant; nonionic surfactants as a smoothing agent or a surface tension adjuster; a disinfectant; a perfume; and a deodorant.

The absorbent layer comprises a single layer or a plurality of layers. As needed, a water absorbing paper or a cotton-like pulp layer is superimposed, a liquid permeable top sheet or a non-woven fabric is arranged on the surface, a liquid-impermeable back sheet is arranged on the back surface, and a gather tape or a tape for mounting on a human body is further provided so as to produce an absorbent material such as a disposable diaper. The material and the kind of a liquid-permeable top sheet, a liquid-impermeable back sheet, a gather tape or a tape for mounting on a human body, and the production method of the absorbent material are not particularly limited, and thus known materials or methods that have been conventionally used in the production of an absorbent material can be used.

The present invention will be further explained with reference to Examples and Comparative Examples, but the present invention is not limited thereto. The absorbency of a model diaper, the absorption rate, the diffusion area, and the surface dryness were measured in the below-mentioned method. Hereinafter "%" denotes "% by mass" and "parts" denotes "parts by mass" unless otherwise specified.

Absorbency: A model diaper was placed horizontally on a metal screen of 12 mesh. Synthetic urine was continuously injected at the center of the model diaper at the rate of 150 ml/minute until the liquid leaked out from the both edges. After draining for 10 minutes by inclining the diaper together with the metal screen at an angle of 30 degrees, the mass was measured and the increased mass was defined as the absorbency.

Absorption rate: An acrylic plate (weight 0.5 kg) having the same area as the model diaper, attaching a cylinder (inner diameter of 3 cm, length of 20 cm) on the center of the place and having a hole with an inner diameter of 3 cm at the center such that the hole contacted with the cylinder is prepared. The acrylic plate is placed on the model paper diaper. Further a load of 4.5 kg is applied onto the acrylic plate (total load 5 kg). 80 ml of synthetic urine (colored with blue ink) was poured into the cylinder. After 30 minutes, a further 80 ml of the synthetic urine was poured for the second dose. Similarly, 30 minutes later, a further 80 ml of the synthetic urine was poured for the third dose. The absorption time of the synthetic urine at the third dose was measured and defined as the absorption rate.

Diffusion area: After measuring the absorption rate of the third dose, the area of the absorbed synthetic urine horizontally spread was measured and defined as the diffusion area.

Surface dryness: After measuring the diffusion area, the dry feeling of the model diaper surface was judged by finger toughing of 10 panelists with the below-mentioned four criteria. The average of the 10 panelists was determined and defined as the surface dryness.

⊚: Excellent dry feeling
○: Dry feeling at a satisfactory level with slight wetting
Δ: Wetting state with poor dry feeling
X: Wet state without dry feeling PRODUCTION EXAMPLE 1 (Production of Water Absorbing Agent)

77 g of sodium acrylate, 23 g of acrylic acid, 0.4 g of N,N'-methylene bisacrylamide and 296 g of deionized water were placed in a 1 liter-glass reaction container and the contents were maintained at 5° C. while stirring.

After introducing nitrogen into the contents so as to have the dissolved oxygen content of 1 ppm or less, 1 g of a 1% aqueous solution of hydrogen peroxide, 1.2 g of a 0.2% aqueous solution of ascorbic acid, and 2.5 g of a 2% aqueous solution of 2,2'-azobisamidinopropane dihydrochloride were added and mixed for initializing the polymerization. An aqueous gel polymer ① was obtained after polymerization for about 6 hours.

While stirring the aqueous gel polymer ① with a kneader, 3 g of a 1% aqueous solution of ethylene glycol diglycidyl ether was added and homogeneously stirred.

The aqueous gel was dried with hot air at 130 to 150° C., pulverized, and the particle size distribution was adjusted to have a two-peak mode distribution as mentioned below so as to obtain water absorbing agents (a) to (e). The results of measuring the performance of the water absorbing agents (a) to (e) are shown in Table 3.

Figure 1:
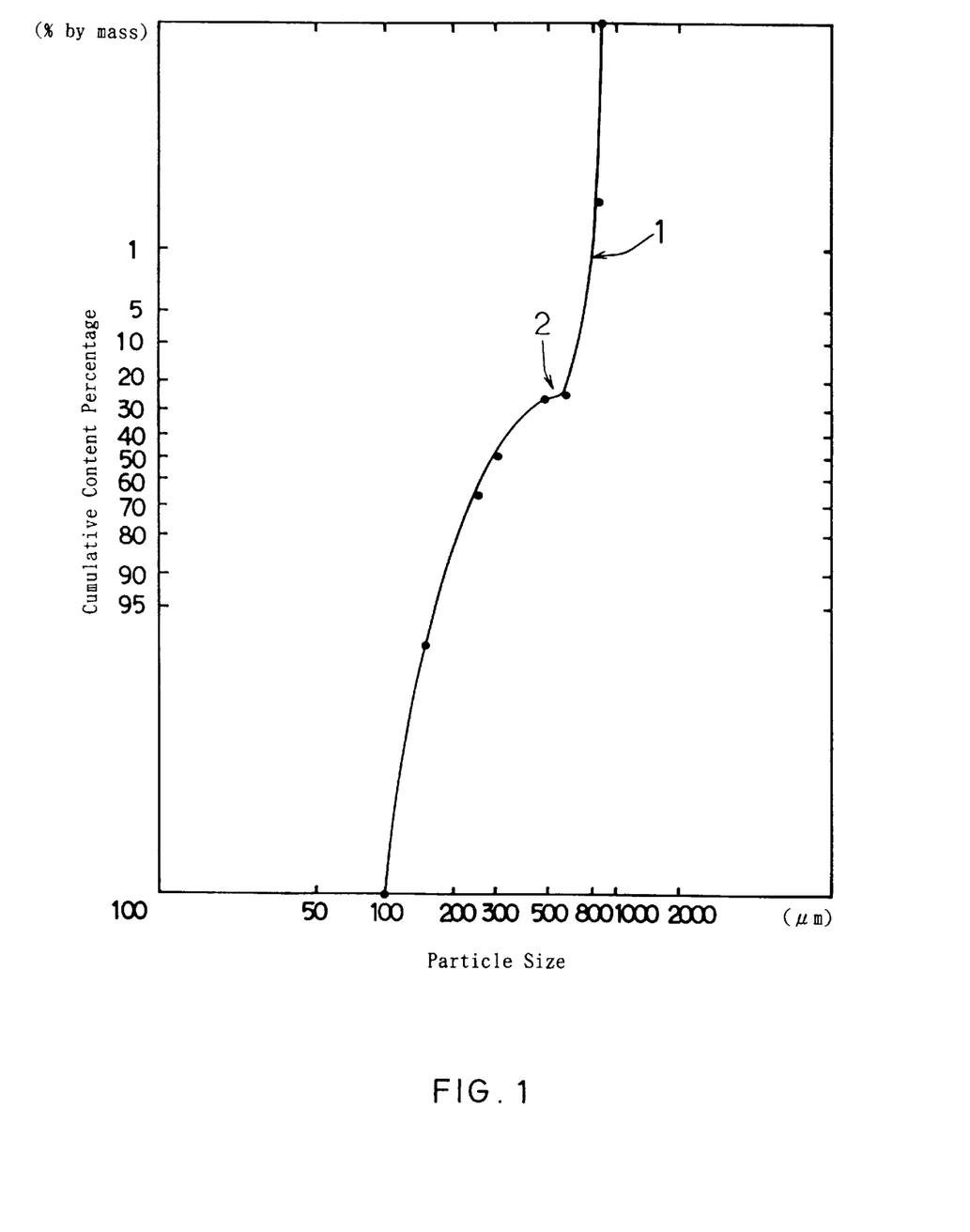
FIG. 1 is a graph prepared by plotting the mass cumulative content percentage of the particle size distribution of the water absorbing agent (a) obtained in Production Example 1 from the larger side of the particle size of the particle size distribution on a logarithmic normal probability paper.
Figure 2:
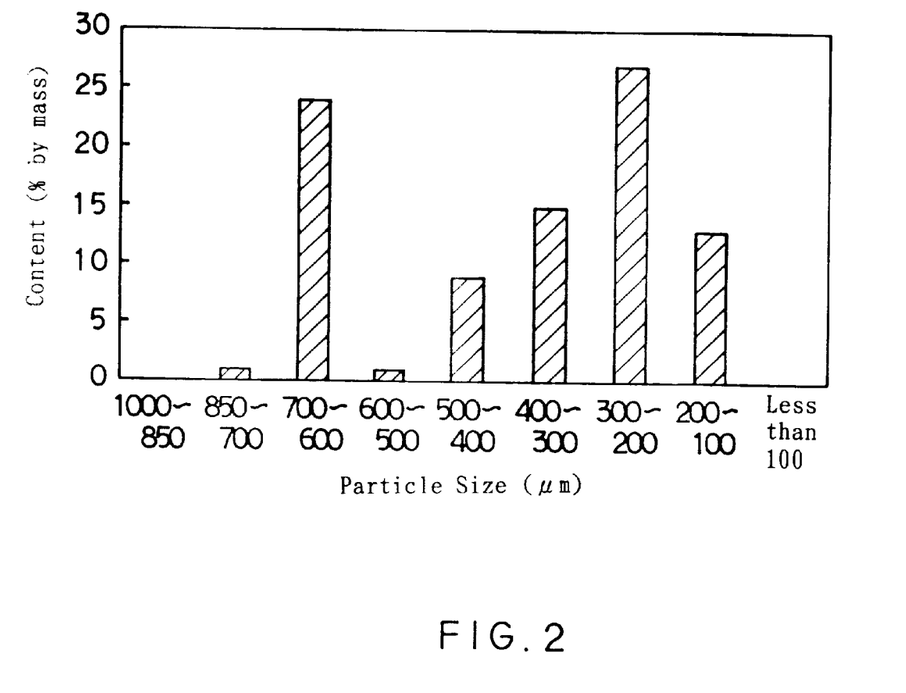
FIG. 2 is a graph prepared by plotting the contents of each particle size range of 100 μm from the graph of the logarithmic normal probability paper in FIG. 1.

The particle size distribution of the water absorbing agents (a) to (e) were measured and plotted in a logarithmic normal probability paper to calculate the content ratio of each particle range to have the results shown in Table 1. As an example of the measurement, the results of plotting the particle size distribution of the water absorbing agent (a) in a logarithmic normal probability paper are shown in FIG. 1. As shown in FIG. 1, the inflection point exists at 550 µm. FIG. 2 is a bar graph, which shows a two-peak mode distribution, prepared by reading out the content in brackets per 100 µm from the graph on the logarithmic normal probability paper in FIG. 1 and showing the content by mass of each particle size range.

TABLE 1

|  | (a) | (b) | (c) | (d) | (e) |
|---|---|---|---|---|---|
| Content (%) of 850 µm or more | 0 | 0 | 0 | 0 | 0 |
| Content from 850 to 600 µm (with the peak at about 700 µm) | 25 | 40 | 60 | 75 | 40 |
| Content from 600 to 400 µm | 10 | 10 | 10 | 10 | 18 |
| Content from 400 to 100 µm (with the peak at about 300 µm) | 65 | 50 | 30 | 15 | 42 |
| Content less than 100 µm | 0 | 0 | 0 | 0 | 0 |
| Position of the inflection point (µm) | 550 | 550 | 425 | 550 | 425 |

NOTE) The content from 850 to 600 µm denotes the content of particles having a size less than 850 µm and 600 µm or more. The same is applied to the content from 600 to 400 µm and the content from 400 to 100 µm.

PRODUCTION EXAMPLE 2 (Production of Water Absorbing Agent)

100 g of acrylic acid, 0.4 g of N,N'-methylene bisacrylamide and 330 g of deionized water were placed in a 1 liter-glass reaction container and the content was maintained at 5° C. while stirring.

After introducing nitrogen into the content so as to have the dissolved oxygen content of 1 ppm or less, 1 g of a 1% aqueous solution of hydrogen peroxide, 1.2 g of a 0.2% aqueous solution of ascorbic acid, and 2.5 g of a 2% aqueous solution of 2,2'-azobisamidinopropane dihydrochloride were added and mixed for initializing the polymerization. An aqueous gel polymer ② was obtained after polymerization for about 6 hours.

While extruding and stirring the aqueous gel polymer ② with an extruder having a perforated plate, 114 g of a 35% aqueous solution of sodium hydroxide were added at the vicinity of the extruder entrance and homogeneously mixed so as to have an aqueous gel with 72 mole % of acrylic acid neutralized.

The aqueous gel was dried with hot air at 130 to 150° C., pulverized, and the particle size distribution was adjusted to have a two-peak mode distribution as in (b) of Production Example 1 so as to obtain a water absorbing agent (f). The results of measuring the performance of the water absorbing agent (f) are shown in Table 3.

PRODUCTION EXAMPLE 3 (Production of Water Absorbing Agent)

While stirring 100 g of the water absorbing agent obtained in Production Example 1 at a high speed, 2 g of a 5% aqueous solution of ethylene glycol diglycidyl ether were sprayed homogeneously, followed by a heat treatment at about 140° C. for 30 minutes so as to obtain a water absorbing agent (g) with the surface crosslinked.

The particle size distribution of (g) was adjusted in the same manner as (b) and (f). The results of measuring the performance of the water absorbing agent (g) are shown in Table 3.

PRODUCTION EXAMPLE 4 (Production of Water Absorbing Agent)

In the same process as Production Example 1 except that the amount of a 1% aqueous solution of ethylene glycol diglycidyl ether to be added to the aqueous gel polymer ① was changed from 3 g to 20 g, a water absorbing agent (h) was obtained. The particle size distribution of (h) was adjusted in the same manner as (b) of Production Example 1. The results of measuring the performance of the water absorbing agent (h) are shown in Table 3.

PRODUCTION EXAMPLE 5 (Production of Water Absorbing Agent)

In the same process as Production Example 1 except that the amount of N,N'-methylene bisacrylamide was changed from 0.4 g to 0.2 g, a water absorbing agent (i) was obtained. The particle size distribution of (i) was adjusted in the same manner as (b) of Production Example 1. The results of measuring the performance of the water absorbing agent (i) are shown in Table 3.

COMPARATIVE PRODUCTION EXAMPLE 1 (Production of Comparative Water Absorbing Agent)

In the same process as Production Example 1 except that the particle size distribution was adjusted as mentioned below, comparative water absorbing agents (a') to (d') were obtained. (a') to (c') have a conventional one-peak mode particle size distribution. (d') has a particle size distribution close to a two-peak mode distribution, but the content in the 600 to 400 µm bracket at nadir is comparatively large. The results of measuring the performance of the comparative water absorbing agents (a') to (d') are shown in Table 4. The particle size distribution of the comparative water absorbing agents (a') to (d') were measured and plotted in a logarithmic normal probability paper to calculate the content ratio of each particle range to have the results shown in Table 2.

TABLE 2

|  | (a') | (b') | (c') | (d') |
|---|---|---|---|---|
| Content (%) of 850 µm or more | 0 | 0 | 0 | 0 |
| Content from 850 to 600 µm | 30 | 15 | 75 | 40 |
| Content from 600 to 400 µm | 40 | 30 | 20 | 25 |

TABLE 2-continued

|  | (a') | (b') | (c') | (d') |
|---|---|---|---|---|
| Content from 400 to 100 µm | 30 | 55 | 5 | 35 |
| Content less than 100 µm | 0 | 0 | 0 | 0 |
| Position of the inflection point (µm) | None | None | None | 150 |

NOTE) The definition of the content from 850 to 600 µm, the content from 600 to 400 µm and the content from 400 to 100 µm is the same as the above-mentioned Production Example 1.

COMPARATIVE PRODUCTION EXAMPLE 2
(Production of Comparative Water Absorbing Agent)

In the same process as Production Example 1 except that the amount of a 1% aqueous solution of ethylene glycol diglycidyl ether to be added to the aqueous gel polymer ① was changed from 3 g to 20 g, a comparative water absorbing agent (e') was obtained. The particle size distribution of (e') was adjusted in the same manner as (b') of Comparative Production Example 1. The results of measuring the performance of the comparative water absorbing agent (e') are shown in Table 4.

COMPARATIVE PRODUCTION EXAMPLE 3
(Production of Comparative Water Absorbing Agent)

In the same process as Comparative Production Example 1 except that the amount of N,N'-methylenebisacrylamide was changed from 0.4 g to 0.2 g, a comparative water absorbing agent (f') was obtained. The particle size distribution of (f') was adjusted in the same manner as (b') of Comparative Production Example 1. The results of measuring the performance of the comparative water absorbing agent (f') are shown in Table 4.

EXAMPLE 1 TO 9

A mixture obtained by mixing 100 parts of fluff pulp and 100 parts of one of the water absorbing agents (a) to (i) of the present invention obtained in Production Examples 1 to 5 with an air blender was evenly spread so as to have the basis weight of about 400 g/m², and pressed with a 5 kg/cm² pressure for 30 seconds to obtain absorbent layers "a" to "i" of Examples 1 to 9.

EXAMPLE 10

After forming a layer of 50 parts of fluff pulp, 100 parts of the water absorbing agent (b) obtained in Production Example 1 was evenly spread, and a layer of 50 parts of fluff pulp was further superimposed thereon to have a sandwich structure, and pressed with a 5 kg/cm² pressure for 30 seconds to obtain an absorbent layer "j".

EXAMPLE 11

A mixture obtained by mixing 100 parts of fluff pulp and 160 parts of the water absorbing agent (b) obtained in Production Example 1 with an air blender was evenly spread so as to have the basis weight of about 400 g/m², and pressed with a 5 kg/cm² pressure for 30 seconds to obtain an absorbent layer "k".

EXAMPLE 12

A mixture obtained by mixing 100 parts of fluff pulp and 50 parts of the water absorbing agent (b) obtained in Production Example 1 with an air blender was evenly spread so as to have the basis weight of about 400 g/m², and pressed with a 5 kg/cm² pressure for 30 seconds to obtain an absorbent layer "m".

EXAMPLE 13

In the same process as Example 2 except that 100 parts of fluff pulp was replaced by 30 parts of a sheath & core type conjugated fiber comprising a core component of polypropylene and a sheath component of polyethylene ("ES fiber EAC" produced by CHISSO CORPORATION) and 70 parts of fluff pulp, an absorbent layer "n" was obtained.

COMPARATIVE EXAMPLES 1 TO 6

A mixture obtained by mixing 100 parts of fluff pulp and 100 parts of one of the comparative water absorbing agents (a') to (f') obtained in Comparative Production Examples 1 to 3 with an air blender was evenly spread so as to have the basis weight of about 400 g/m², and pressed with a 5 kg/cm² pressure for 30 seconds to obtain absorbent layers "a'" to "f'" of Comparative Examples 1 to 6.

COMPARATIVE EXAMPLE 7

A mixture obtained by mixing 100 parts of fluff pulp and 17 parts of the water absorbing agent (b) obtained in Production Example 1 with an air blender was evenly spread so as to have the basis weight of about 500 g/m², and pressed with a 5 kg/cm² pressure for 30 seconds to obtain a comparative absorbent layer "g'".

TEST EXAMPLE

Model diapers were produced with the absorbent layers obtained in Examples 1 to 13 and Comparative Examples 1 to 7 cut in a rectangular shape of 14 cm×36 cm, with water absorbing papers of the same size applied on both the top side and back side for each absorbent layer, a polyethylene sheet used in a commercial disposable diaper on the rear side and a non-woven fabric on the surface. The results of evaluating these model diapers in terms of the absorption rate, the diffusion area, and the absorbency are shown in Table 3 for those utilizing the absorbent layers of Examples 1 to 13 and in Table 4 for those utilizing the absorbent layers of Comparative Examples 1 to 7.

TABLE 3

| | (A) Performance of a Water Absorbing Agent | | | | (B) Performance of a Model Diaper | | |
|---|---|---|---|---|---|---|---|
| (1) Water Absorbing Agent | (2) Absorbency under Pressure Free State (g/g) | (3) Absorbency under Load (g/g) | (4) Gel Elasticity Modulus (×10³ N/m²) | (5) Absorbency (g/sheet) | (6) Absorption rate (second) | (7) Diffusion Area (cm²) | (8) Surface Dryness |
| Ex. 1 | 57 | 30 | 9 | 588 | 25 | 403 | ⊚ |
| 2 | 57 | 30 | 9 | 593 | 23 | 416 | ⊚ |
| 3 | 57 | 30 | 9 | 590 | 21 | 422 | ⊚ |
| 4 | 57 | 30 | 9 | 585 | 18 | 438 | ⊚ |
| 5 | 57 | 30 | 9 | 591 | 26 | 410 | ⊚ |
| 6 | 62 | 28 | 6 | 651 | 25 | 418 | ⊚ |
| 7 | 60 | 33 | 8 | 599 | 20 | 424 | ⊚ |
| 8 | 47 | 26 | 16 | 491 | 23 | 408 | o to Δ |
| 9 | 68 | 12 | 3 | 690 | 25 | 400 | o to Δ |
| 10 | 57 | 30 | 9 | 582 | 19 | 402 | ⊚ to o |
| 11 | 57 | 30 | 9 | 752 | 28 | 412 | ⊚ |
| 12 | 57 | 30 | 9 | 445 | 18 | 428 | o |
| 13 | 57 | 30 | 9 | 590 | 27 | 422 | ⊚ |

TABLE 4

| | (A) Performance of Comparative Water Absorbing Agent | | | | (B) Performance of a Model Diaper | | |
|---|---|---|---|---|---|---|---|
| (1) Comparative Water Absorbing Agent | (2) Absorbency under Pressure Free State (g/g) | (3) Absorbency under Load (g/g) | (4) Gel Elasticity Modulus (×10³ N/m²) | (5) Absorbency (g/sheet) | (6) Absorption rate (second) | (7) Diffusion Area (cm²) | (8) Surface Dryness |
| Comp Ex. 1 | 57 | 30 | 9 | 585 | 45 | 362 | Δ to x |
| 2 | 57 | 30 | 9 | 582 | 51 | 323 | x |
| 3 | 57 | 30 | 9 | 568 | 68 | 387 | x |
| 4 | 57 | 30 | 9 | 582 | 41 | 360 | Δ |
| 5 | 47 | 26 | 16 | 488 | 77 | 345 | x |
| 6 | 68 | 13 | 3 | 681 | 83 | 316 | X |
| 7 | 57 | 30 | 9 | 817 | 38 | 245 | x |

Absorbent materials using water absorbing agents of the present invention have the following characteristics and effects:

① A water absorbing agent of the present invention can be produced easily with ordinary equipment for producing a water absorbent resin.

② Since the liquid diffusion is good and the absorption rate is excellent, the absorbent material obtained by using the water absorbing agent of the present invention has excellent surface dryness after liquid absorption and can reduce the risk of leakage.

③ Since the gel elasticity modulus is at a proper level, excellent absorption performance and absorption rate can be provided for repeated absorption over a long time.

④ In the case of producing an absorbent layer with drum forming type equipment, clogging of water absorbent resin particles in the screen mesh or loss caused by falling off of the times of water absorbent resin particles from the screen mesh can be reduced. In the drum forming type absorbent layer production method, a drum provided with cut-out portions of the same planar shape of the absorbent layer on the periphery with screen meshes fixed on the cut-out portions is used such that a mixture of pulp and a water absorbing agent is sprinkled on the drum from the upper direction and is subjected to vacuum from the inside of the drum to be accumulated on the screen meshes. That is, particles having a similar size to the mesh opening of a screen mesh can easily clog into the screen mesh, and particles having a size smaller than the mesh opening of a screen mesh fall off through the screen mesh to be loss.

⑤ Since the anti-caking property under humid condition is good, a good operativity can be achieved even in a highly humid condition.

Since the above-mentioned effect can be achieved, a water absorbing agent of the present invention can be preferably applied in disposable diapers (diapers for infants or adults). In particular, it can be applied preferably in a thin type disposable diaper having a large ratio of a water absorbent resin/a fibrous material.

Furthermore, it can be preferably used in other hygienic materials (sanitary napkins, incontinence pads, mother breast pads, under pads for surgical operations, parturition mats, dressing materials for injury, pet sheets), and various absorbing sheets (freshness retaining sheets, drip absorbing sheets, anti-dewing sheets, sheets for rearing a young paddy rice plant, aging sheets for concrete, oil/water separation sheets, fire extinguishing sheets).

What is claimed is:

1. A water absorbing agent comprising water absorbent resin particles (A) having a particle size of 1000 μm or less, with a two-peak mode particle size distribution, and having an inflection point in the range of 750 to 250 μm particle size, prepared by plotting the mass cumulative content percentage from the larger side of the particle size of the particle size distribution on a logarithmic normal probability paper, wherein particles (A) have a particle size distribution comprising 15 to 75% by mass of particles having a particle size of from 600 μm to less than 1000 μm with a first peak existing therein, 15 to 70% by mass of particles having a particle size of 100 μm to less than 400 μm with a second peak existing therein, 5% or less by mass of particles having a particle size of less than 100 μm, and less than 20% by mass of particles having a particle size of 400 to less than 600 μm, wherein particles (A) are all produced by pulverizing the same water absorbent resin.

2. The water absorbing agent according to claim 1, wherein the vicinity of the surface of the water absorbent resin particles (A) are crosslinked.

3. The water absorbing agent according to claim 1, wherein the water absorbent resin particles (A) have an absorbency under load and an absorbency under a pressure free state with respect to physiological saline solution of 45 to 75 g/g and 25 to 50 g/g, respectively, and a gel elasticity modulus of a 40-times swelled gel of (A) after absorbing physiological saline solution of 2500 to 15000 N/m².

4. An absorbent material comprising a liquid-permeable top sheet, a liquid-impermeable back sheet, and an absorbent layer provided between the top and back sheets, wherein the absorbent layer comprises the water absorbing agent (A) according to claim 1 and a fibrous material (B) with a ratio of (A) to (B) being from (15 to 70):(85 to 30) based on the mass.

* * * * *